United States Patent
Wan et al.

(10) Patent No.: US 9,788,815 B2
(45) Date of Patent: Oct. 17, 2017

(54) CONTRAST IMAGING METHOD BASED ON WIDE BEAM AND METHOD FOR EXTRACTING PERFUSION TIME-INTENSITY CURVE

(71) Applicant: XI'AN JIAOTONG UNIVERSITY, Xi'an, Shaanxi (CN)

(72) Inventors: Mingxi Wan, Shaanxi (CN); Diya Wang, Shaanxi (CN); Xuan Yang, Shaanxi (CN); Yu Zhai, Shaanxi (CN); Hui Zhong, Shaanxi (CN)

(73) Assignee: XI'AN JIAOTONG UNIVERSITY, Xi'an, Shaanxi (CN)

(*) Notice: Subject to any disclaimer, the term of this patent is extended or adjusted under 35 U.S.C. 154(b) by 407 days.

(21) Appl. No.: 14/438,936

(22) PCT Filed: May 29, 2014

(86) PCT No.: PCT/CN2014/078732
§ 371 (c)(1),
(2) Date: Apr. 28, 2015

(87) PCT Pub. No.: WO2015/131453
PCT Pub. Date: Sep. 11, 2015

(65) Prior Publication Data
US 2016/0242741 A1 Aug. 25, 2016

(30) Foreign Application Priority Data
Mar. 6, 2014 (CN) .......................... 2014 1 0081743

(51) Int. Cl.
*A61B 8/08* (2006.01)
*A61B 8/14* (2006.01)
*A61B 8/06* (2006.01)

(52) U.S. Cl.
CPC .............. *A61B 8/5223* (2013.01); *A61B 8/06* (2013.01); *A61B 8/14* (2013.01); *A61B 8/481* (2013.01)

(58) Field of Classification Search
CPC .. A61B 8/06; A61B 8/14; A61B 8/481; A61B 8/5223
See application file for complete search history.

(56) References Cited

FOREIGN PATENT DOCUMENTS

| CN | 103330576 A | * 10/2013 |
| CN | 103381096 A | * 11/2013 |

* cited by examiner

*Primary Examiner* — Michael Rozanski

(57) ABSTRACT

A contrast imaging method based on a wide beam and a method for extracting a perfusion time-intensity curve (TIC) are provided to increase contrast-to-tissue ratio (CTR) through the contrast imaging method based on the wide beam via a pulse inversion microbubble wavelet transform sum squared differences decorrelation (PIWSSD). An auto adaptive analysis method about rapidly and accurately extracting a TIC tendency of the contrast imaging method based on the wide beam is also provided to overcome limitations of a decrease in the CTR of the contrast imaging based on the wide beam and a decrease in SCR of the perfusion TIC. The present invention plays an important role in effectively reducing an ultrasound contrast imaging acoustic power and a contrast microbubble perfusion concentration, reducing potential threat to human body, acquiring a contrast image with the high CTR, and accurately evaluating and diagnosing blood perfusion.

10 Claims, 6 Drawing Sheets

CONTRAST IMAGING METHOD BASED ON WIDE BEAM AND METHOD FOR EXTRACTING PERFUSION TIME-INTENSITY CURVE

CROSS REFERENCE OF RELATED APPLICATION

This is a U.S. National Stage under 35 U.S.C 371 of the International Application PCT/CN2014/078732, filed May 29, 2014, which claims priority under 35 U.S.C. 119(a-d) to CN 201410081743.6, filed Mar. 6, 2014.

BACKGROUND OF THE PRESENT INVENTION

Field of Invention

The present invention relates to a field of ultrasound imaging, and more particularly to a contrast imaging method based on a wide beam and a method for extracting a perfusion time-intensity curve (TIC).

Description of Related Arts

The conventional B-mode ultrasonography images via acoustic focus of the scanning lines one by one, at the frame rate about 60 Hz. In the meantime, in order to clinically obtain the high resolved ultrasonic image and imaging depth, the relatively higher acoustic power is usually employed, which may not only impair the tissues but also enhance damages to the microbubbles, so as to decrease the contrast-to-tissue ratio (CTR) to certain extent. Moreover, the conventional scanning mode line-by-line causes multiple times of damages to the microbubbles, which forces to clinically further enhance the perfusion concentration of the contrast agent in order to maintain a relatively high CTR. It is a clinical founding that the over high acoustic power and the over high concentration of the contrast agent may potentially threat the health of the human body, which restricts the further application of the ultrasound contrast imaging in the clinical medicine. Meanwhile, for the B-mode contrast imaging in vivo at the low frame rate, the respiratory movement and the organ involuntary peristalsis would generate the false movement track. The false movement track results in the apparent distinctions between the former frame and the latter frame, and thus affects the imaging quality, the accurate extracting of the subsequent TIC and the reliable evaluation of perfusion. Besides, the low frame rate has a poor performance in catching the rapidly-moving organ, resulting in the absence of the corresponding evaluation and the insensitivity to the instantaneous movement information. Accordingly, the rapid high-frame-rate contrast imaging emerged.

Conventionally, the widely applied ultrasound contrast imaging technologies basically employ the linearity or the non-linearity of the microbubble oscillation, such as the harmonic imaging, the harmonic power Doppler imaging, the pulse inversion imaging and the pulse inversion harmonic imaging. The high-frame-rate plane wave imaging enables the observation to the instantaneous change of the microbubbles and the monitoring to the rapid movement of the perfusion area, and contributes to the innovation in contrast mechanisms.

Therein, the pulse inversion (PI) is the common manner for obtaining the relatively high signal-to-noise ratio (SNR) through the apparent echo differences caused by the non-linearity of the microbubbles and the linearity of the tissues. The microbubble wavelet transform, based on taking advantage of the microbubble echo information as much as possible, suppresses the impact brought by the non-linear acoustic feature of the tissues to further increase the CTR and the detection sensitivity of the contrast microbubbles. The decorrelation is the manner for improving the CTR, by setting the decorrelation threshold based on the decorrelation difference of the contrast microbubbles and the surrounding tissues between the neighboring echo signals of the video frequency (VF) signals. The decorrelation not only has a relatively high sensitivity to the movement of the tissues, but also remedies the limitation of the PI and the microbubbles wavelet transform on the radio frequency (RF) signals by processing the VF signals.

The scattered echo signals obtained from the contrast imaging contain a series of physiological information. During the specific operations, the TIC is usually extracted to obtain time distribution information, such as the blood flow velocity, the blood volume and the hemodynamics. The echo signal enhancement induced by the microbubbles is proportional to the concentration, and thus is also proportional to the blood volume of the tissues, which converts the time distribution information denominated by the TIC into the spatial distribution information and promotes the development of the perfusion parametric estimation. Thus, a precise and rapid extracting of the TIC tendency plays an important role in the image quality of the parametric imaging and the authenticity of the evaluation and diagnosis of the blood perfusion.

There are various conventional processing methods after the extracting of the TIC, such as the baseline zeroing, the interpolation processing, the filtering processing and the function fitting or the perfusion model fitting. The wide beam contrast imaging is different from the conventional narrow beam contrast imaging, so as to greatly restrict the application of the conventional TIC processing methods, especially the application of the TIC perfusion model fitting. Accordingly, the present invention adopts a Detrended Fluctuation Analysis (DFA) fitting method, which not only divides TIC data into sections with consideration of an induced weight on an overlapped section by the data before and after a fitting section, and executes an auto adaptive non-linear polynomial fitting. Nevertheless, despite of being able to completely extract the TIC overall tendency, the conventional TIC processing methods, mostly based on the integral data fitting and the point-by-point processing, are still unable to accurately fit upon the partial dynamic tendency; moreover, due to the few original TIC data at the low frame rate, the single point exerts a relatively big weight upon the final fitting result. It is difficult for the subsequent processing to completely eliminate the impact on the overall TIC tendency brought by the partial singular points. In order to ensure the accuracy of the TIC fitting, it is also difficult to lower the time cost of the point-by-point processing.

SUMMARY OF THE PRESENT INVENTION

An object of the present invention is to provide a contrast imaging method based on a wide beam and a method for extracting a perfusion TIC, which increase CTR through the contrast imaging method based on the wide beam via PIWSSD. The present invention also provides an auto adaptive analysis method about rapidly and accurately extracting a TIC tendency of the contrast imaging method based on the wide beam, so as to overcome limitations of a decrease in the CTR of the contrast imaging based on the wide beam and a decrease in SCR of the perfusion TIC.

Accordingly, in order to accomplish the above objects, the present invention adopts the following technical solutions.

A contrast imaging method based on a wide beam comprises steps of:

(1) constructing microbubble mother wavelets of phase 0/180 for a wide beam contrast imaging, according to a Herring-Trilling microbubble oscillation equation modified by Morgan model;

(2) automatically emitting wide beam RF signals, and receiving the wide beam RF signals which are reflected back by an object, by ultrasound array transducers; processing the wide beam RF signals with phase 0/180 which are received by the ultrasound array transducers, with a wavelet correlation analysis based on the microbubble mother wavelets obtained in the step (1); extracting a maximum wavelet correlation coefficient at an optimal wavelet transform scale; and constructing a pulse inversion microbubble wavelet transform images matrix (PIW images matrix); and (3) constructing a pulse inversion sum squared differences (PISSD) thresholds matrix, determining decorrelation thresholds of the PIW images matrix of the step (2), and then obtaining a pulse inversion microbubble wavelet transform sum squared differences decorrelation (PIWSSD) image of the wide beam contrast imaging.

The step (1) comprises steps of:

(a) driving the Herring-Trilling microbubble oscillation equation, showed as equation (1), respectively with scanning acoustic pressure curves of phase 0/180 with a wide beam; then obtaining a change curve of a microbubble oscillation radius with time, a corresponding radial oscillation velocity and a corresponding acceleration;

(b) substituting the obtained change curve, the radial oscillation velocity and the acceleration into an equation (2) to obtain a microbubble oscillation amplitude acoustic pressure waveform under the wide beam;

(c) processing the microbubble oscillation amplitude acoustic pressure waveform under the wide beam, into the microbubble mother wavelets of the phase 0/180 for the wide beam contrast imaging, through a band-pass filtering and a normalization.

$$\rho R\ddot{R} + \frac{3}{2}\rho \dot{R}^2 = \qquad (1)$$

$$\left[P_0 + \frac{2\sigma}{R_0} + \frac{2\chi}{R_0}\right]\left[\frac{R_0}{R}\right]^{3\gamma}\left[1 - \frac{3\gamma}{c}\dot{R}\right] - \frac{4\mu\dot{R}}{R} - \frac{2\sigma}{R}\left[1 - \frac{1}{c}\dot{R}\right] -$$

$$\frac{2\chi}{R}\left(\frac{R_0}{R}\right)^2\left(1 - \frac{3}{c}\dot{R}\right) - 12\mu_{sh}\varepsilon\frac{\dot{R}}{R(R\cdot\varepsilon)} - [P_0 + P_{driv}(t)]$$

$$P = \rho r^{-1}\left(R^2\ddot{R} + R\dot{R}^2\right) \qquad (2)$$

The step of constructing the PIW images matrix in the step (2) comprises steps of:

(d) at a finish of receiving the wide beam RF signals, selecting an appropriate scale, and respectively processing echo signals of the RF signals of the phase 0 and the phase 180 with the wavelet correlation analysis based on the microbubble mother wavelets of the phase 0/180 constructed in the step (1), so as to obtain a series of the wavelet correlation coefficients;

(e) for the echo signals of the phase 0 and the phase 180, respectively selecting all wavelet correlation coefficients, at the scale where the maximum wavelet correlation coefficient is located, to be return values for denominating the echo signals of the RF signals of the phase 0 and the phase 180; and (f) summing the wavelet correlation coefficients for denominating the echo signals of the RF signals in the echo signals of the phase 0 and the phase 180, and obtaining the PIW images matrix via a Hilbert envelope-demodulation.

The step (3) comprises steps of:

(g) dividing the echo signals denominated by the wavelet correlation coefficients of the phase 0 and the phase 180, obtained by the step (2), into a plurality of sampling windows, wherein each sampling window has a length of $L_w$ and is mutually overlapped by an overlap length of $L_o$;

(h) providing a PISSD algorithm showed as equation (3), wherein the PISSD thresholds matrix is determined by a total number of sampling points N, an ordinal number of the sampling windows n, the length of each sampling window $L_w$, the overlap length of each sampling window $L_o$, a sampling window function w[ ] and the wavelet correlation coefficients of the phase 0 and the phase 180:

$$PISSD(n) = \frac{1}{L_w}\sum_{k=1+(n-1)\Delta}^{L_o+n\Delta}(w[s_{f1}(k)] + w[s_{f2}(k)]])^2 \qquad (3)$$

$$n = 1, 2, \ldots, (N - L_w)/\Delta + 1, \Delta = L_w - L_o, L_o < L_w,$$

wherein $s_{f1}(k)$ and $s_{f2}(k)$ are respectively the echo signals denominated by the wavelet correlation coefficients of the phase 0 and the phase 180 obtained by the step (2);

(i) constructing a two-dimensional PISSD thresholds matrix which illustrates a decorrelation degree of a tissues background, with the PISSD algorithm of step (h);

(j) defining four types of thresholds based on the PISSD thresholds matrix: a uniform threshold, a divided threshold, a lower combined threshold and a higher combined threshold; wherein:

the uniform threshold is a sum of a mean and a standard deviation of the PISSD matrix;

the PISSD matrix is divided into M sections with the same size along a scanning beam direction, the sum of the mean and the standard deviation of PISSD within each section is the divided threshold corresponding to each section;

the lower combined threshold (LCT) is showed in equation (4):

$$LCT(i, j) = \begin{cases} DT(i, j), & DT(i, j) \le UT \\ UT, & DT > (i, j) \end{cases} \qquad (4)$$

$$i = 1, 2, \ldots, N_s, j = 1, 2, \ldots, N_l;$$

and the higher combined threshold (HCT) is showed in equation (5):

$$HCT(i, j) = \begin{cases} DT(i, j), & DT(i, j) \ge UT \\ UT, & DT(i, j) < UT \end{cases} \qquad (5)$$

$$i = 1, 2, \ldots, N_s, j = 1, 2, \ldots, N_l;$$

(k) based on the four types of thresholds of the step (j), inputting the PISSD thresholds matrix, a PISSD images matrix and the PIW images matrix into a PISSD threshold determining module, and then obtaining the PIWSSD image.

Further, the present invention provides a method for extracting a perfusion TIC of the contrast imaging method based on the wide beam, further comprising steps of:

(4) extracting a perfusion TIC of a region of interest (ROI) of the PIWSSD image of the step (3);

(5) constructing a window length order matrix X and a polynomial fitting coefficient matrix Fit for DFA; and (6) processing the TIC, obtained in the step (4), with the DFA to extract a TIC tendency.

The step (5) comprises steps of:

(l) determining the window length order matrix X for the DFA by a length of original TIC data Num, a DFA semi-window-length N and a polynomial fitting order K, and constructing the window length order matrix X for the DFA according to equation (6):

$$X = \begin{bmatrix} x(1)^0 & x(1)^1 & \ldots & x(1)^K \\ \vdots & \vdots & \ddots & \vdots \\ x(2N)^0 & x(2N)^1 & \ldots & x(2N)^K \\ x(2N+1)^0 & x(2N+1)^1 & \ldots & x(2N+1)^K \end{bmatrix}; \quad (6)$$

and (m) determining the polynomial fitting coefficient matrix Fit for the DFA by the length of the original TIC data Num and the DFA semi-window-length N; obtaining an optimal polynomial fitting coefficient matrix P of sections of TIC data with a least squares multiple regression analysis, according to equation (7):

$$P = (X^T X)^{-1} \times X^T \times \quad (7)$$

$$\begin{bmatrix} TIC(1) & \ldots & TIC(2N) & TIC(2N+1) \\ TIC(N+1) & \ldots & TIC(3N) & TIC(3N+1) \\ \vdots & \ddots & \vdots & \vdots \\ TIC(Num-2N) & \ldots & TIC(Num-1) & TIC(Num) \end{bmatrix};$$

and obtaining the polynomial fitting coefficient matrix Fit for the DFA according to equation (8):

$$\text{Fit} = X \times P \quad (8)$$

$$= X(X^T X)^{-1} \times X^T \times$$

$$\begin{bmatrix} TIC(1) & \ldots & TIC(2N) & TIC(2N+1) \\ TIC(N+1) & \ldots & TIC(3N) & TIC(3N+1) \\ \vdots & \ddots & \vdots & \vdots \\ TIC(Num-2N) & \ldots & TIC(Num-1) & TIC(Num) \end{bmatrix}.$$

The step (6) comprises steps of:

(n) judging a rank of the original TIC data to ensure that a row number is larger than a column number, and transposing the original TIC data when the row number of the original TIC data is smaller than the column number of the original TIC data;

(o) dividing the TIC data obtained by the step (n) into 2N+1 sections with the same length, and marking the length of the sections as a window length, wherein each two neighboring sections have N+1 points overlapped;

(p) for each section, selecting optimal K-order polynomials for fitting, wherein a constant and a linear fitting respectively correspond to K=0 and K=1;

(q) constructing the window length order matrix X and the polynomial fitting coefficient matrix Fit for the DFA;

(r) obtaining the optimal polynomial fitting coefficient matrix P of the sections of the TIC data with the least squares multiple regression analysis;

(s) judging whether a whole length of the TIC data is divided by the window length without remainder; if without remainder, obtaining a weighting coefficient of the polynomial linear fitting; if with remainder, firstly weighted fitting a last section of the TIC data whose length is smaller than the window length;

(t) respectively marking the fitted polynomials of the ith section and the (i+1)th section as $y^i(l_1)$ and $y^{i+1}(l_2)$, $l_1$, $l_2=1, \ldots, 2N+1$;

wherein the fitted polynomial of the overlapped section $y^o(l)$ is $y^o(l)=w_1 y^i(l+N)+w_2 y^{i+1}(l)$, $l=1, \ldots, N+1$, wherein the weighting coefficients of the polynomial linear fitting are respectively $w_1=1-(l-1)/N$, $w_2=(l-1)/N$;

(u) successively weighted fitting the data of the overlapped section; and (v) combining results of weighted fitting the last section of the TIC data whose length is smaller than the window length and the sections therebefore, and outputting a TIC after fitting.

A method for evaluating a fitting quality of the TIC after fitting comprises steps of:

(w) selecting a quality of fitting (QOF) as a first evaluation index of an overall tendency of the TIC;

(x) selecting a detailed evaluation index (DEI) as a second evaluation index of the overall tendency of the TIC;

(y) coding via matlab for calculating the QOF and the DEI; and (z) respectively processing the TIC data with the DFA, and calculating out the QOF, the DEI and a runtime.

When the QOF reaches a maximum value of 100%, the TIC after fitting is best fitted. When the QOF is lower than 80%, the TIC after fitting is inaccurately fitted and thus lacks reliability.

The QOF is calculated according to equations (9), (10) and (11):

$$QOF = \left(1 - \frac{SSR_f}{VAR_d}\right) \times 100\%; \quad (9)$$

$$SSR_f = \sum_{t=t_{start}}^{t_{end}} (TIC_f(t) - TIC_d(t))^2; \text{ and} \quad (10)$$

$$VAR_d = \sum_{t=t_{start}}^{t_{end}} \left(TIC_d(t) - \frac{\sum_{t=t_{start}}^{t_{end}} TIC_d(t)}{N}\right)^2; \quad (11)$$

wherein $SSR_f$ is a sum squared residue of the TIC after fitting and a filtering TIC within a fitting interval; $VAR_d$ is a variance of the filtering TIC within the fitting interval; $TIC_f$ is the TIC after fitting and $TIC_d$ is the filtering TIC; $t_{start}$ and $t_{end}$ are a starting point and an ending point of the fitting interval; and N is a number of the sample points within the fitting interval.

The larger DEI indicates the stronger ability of the TIC after fitting to preserve details of the original data. When the DEI is smaller than 0.85, the TIC after fitting distorts against perfusion details and thus lacks reliability.

The DEI is defined as:

$$DEI = \frac{\sum(|TIC_f(t) - TIC_f(t-1)| + |TIC_f(t) - TIC_f(t+1)|)}{\sum(|TIC_d(t) - TIC_d(t-1)| + |TIC_d(t) - TIC_d(t+1)|)}, \quad (12)$$

wherein $TIC_f(t)$ and $TIC_d(t)$ are respectively TIC values before fitting and after fitting; a maximum of the DEI is 1, and a minimum of the DEI is 0.

Compared to conventional arts, the present invention has the following advantages.

The contrast imaging method based on the wide beam, provided by the present invention, is a contrast imaging algorithm for the wide beam contrast imaging, combining a pulse inversion, a microbubble wavelet transform and a decorrelation. The method combines merits of the pulse inversion, the wavelet transform and the decorrelation algorithm, greatly increases the CTR of the wide beam ultrasound contrast imaging, and greatly decreases an acoustic power of the ultrasound transducers while satisfying a requirement for the CTR of the ultrasound contrast image. To certain extent, the present invention reduces potential threat of an ultrasound high acoustic power to human body.

Different from a conventional scanning mode line-by-line, the multiple scanning lines of the wide beam emit and receive simultaneously. At the same frame rate, compared to the conventional mode, the present invention reduces times of damages to the microbubbles by the wide beam, and lowers the acoustic power applied onto the microbubbles, so as to weaken the damages to the microbubbles by the transducers and overcome a high acoustic power and a high contrast concentration of the conventional B-mode ultrasonography. The present invention provides the contrast imaging method based on the wide beam via the pulse inversion, the wavelet transform and the decorrelation, so as to solve the multiple times of damages to the contrast microbubbles by the conventional scanning of the ultrasound transducers line-by-line and offer the clinical application an imaging method ensuring the image quality while reducing a perfusion contrast microbubble concentration.

The present invention further provides the method for extracting the perfusion TIC which is an auto adaptive method for extracting the TIC overall tendency and the partial perfusion tendency, with a higher accuracy, under principles of data division, partial overlap and high-order fitting, involving the evaluation indexes of the overall tendency and the partial details, i.e., the QOF and the DEI.

The TIC under the wide beam has many points, as well as many partial singular points. However, the DFA is characterized in the partial overlap and the high-order fitting, and thus enabled to extract the overall tendency and the partial dynamic tendency to a greatest extent while effectively eliminating the singular points and shorten the runtime, which benefits the TIC of a secondary circulation/perfusion and the TIC with an elongated perfusion time. Therefore, it plays an important role in the blood perfusion evaluation and diagnosis to accomplish rapidly extracting the TIC tendency and obtaining the accurate perfusion information by the pulse inversion wavelet transform decorrelation contrast imaging method under the wide beam plane wave.

Compared to conventional arts, the method for extracting the perfusion TIC, provided by the present invention, extracts the wide beam contrast imaging-TIC tendency at a higher speed. A conventional fitting moves the window length point by point; on the contrary, the DFA of the present invention moves by a relatively larger step size, namely the half-window-length, which shortens the runtime.

The present invention provides the contrast imaging method based on the wide beam and the method for extracting the perfusion TIC which play an important role in effectively reducing the ultrasound contrast imaging acoustic power and the contrast microbubble perfusion concentration, reducing the potential threat to the human body, acquiring the contrast image with the high CTR, and accurately evaluating and diagnosing the blood perfusion.

These and other objectives, features, and advantages of the present invention will become apparent from the following detailed description, the accompanying drawings, and the appended claims.

DETAILED DESCRIPTION OF THE PREFERRED EMBODIMENT

Figure 1:
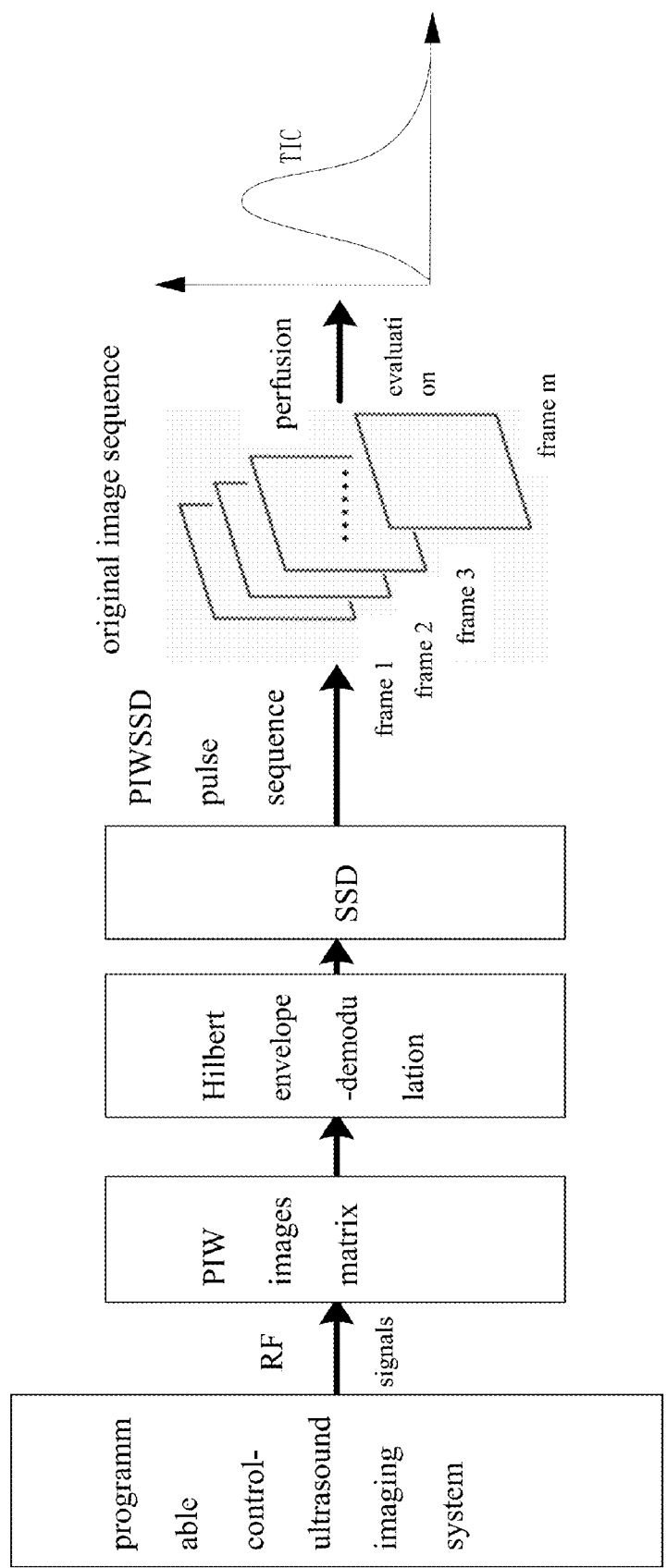
FIG. 1 is a block diagram of a pulse inversion wavelet transform decorrelation wide beam contrast imaging method and a perfusion evaluation method thereof according to a preferred embodiment of the present invention.

One skilled in the art will understand that the embodiment of the present invention as shown in the drawings and described above is exemplary only and not intended to be limiting.

In order to overcome restrictions of a decrease in CTR of a wide beam contrast imaging and a decrease in SCR of a perfusion evaluation TIC, the present invention provides a contrast imaging method based on a wide beam and its method for extracting a perfusion TIC, comprising steps of: firstly improving the CTR by the wide beam contrast imaging method based on PIWSSD; and then, analyzing about rapidly and accurately extracting a wide beam contrast imaging TIC tendency based on the imaging method. The present invention plays an important role in effectively reducing an ultrasound contrast imaging acoustic power and a contrast microbubble perfusion concentration, reducing potential threat to human body, acquiring a contrast image with a high CTR, and accurately evaluating and diagnosing blood perfusion.

Referring to FIG. 1 of the drawings, according to a preferred embodiment of the present invention, a pulse inversion wavelet transform decorrelation wide beam contrast imaging method comprises steps of:

firstly obtaining RF data via an ultrasound imaging system, processing the RF data with a wavelet analysis to obtain a PIW images matrix, and combining a sum squared differences (PISSD) technique, so as to obtain a wide beam PIWSSD image; and then, extracting a perfusion evaluation curve TIC of a ROI of the PIWSSD image; accurately and rapidly extracting a tendency of the TIC for a perfusion evaluation of a wide beam contrast imaging.

The present invention provides a contrast imaging method based on a wide beam, comprising the following steps.

Step (1): constructing mother wavelets of a compression phase and an expansion phase, namely phase 0/180, respectively for a wide beam contrast imaging, according to a Herring-Trilling microbubble oscillation equation modified by Morgan model, as showed in equations (1) and (2):

$$\rho \dot{R} \ddot{R} + \frac{3}{2}\rho \dot{R}^2 = \left[P_0 + \frac{2\sigma}{R_0} + \frac{2\chi}{R_0}\right]\left[\frac{R_0}{R}\right]^{3\gamma}\left[1 - \frac{3\gamma}{c}\dot{R}\right] - \frac{4\mu\dot{R}}{R} - \frac{2\sigma}{R}\left[1 - \frac{1}{c}\dot{R}\right] - \frac{2\chi}{R}\left(\frac{R_0}{R}\right)^2\left(1 - \frac{3}{c}\dot{R}\right) - 12\mu_{sh}\varepsilon\frac{\dot{R}}{R(R\cdot\varepsilon)} - [P_0 + P_{driv}(t)], \text{ and} \tag{1}$$

$$P = \rho r^{-1}\left(R^2\ddot{R} + R\dot{R}^2\right). \tag{2}$$

The step (1) comprises steps of:

(a) driving the Herring-Trilling microbubble oscillation equation, showed as the equation (1), respectively with scanning acoustic pressure curves of phase 0/180 with a wide beam; then obtaining a change curve of a microbubble oscillation radius with time, a corresponding radial oscillation velocity and a corresponding acceleration;

(b) substituting the obtained change curve, the radial oscillation velocity and the acceleration into the equation (2) to obtain a microbubble oscillation amplitude acoustic pressure waveform under the wide beam; and (c) processing the microbubble oscillation amplitude acoustic pressure waveform under the wide beam, into the microbubble mother wavelets of the phase 0/180 for the wide beam contrast imaging, through a band-pass filtering and a normalization.

Table 1 shows a definition and a value of each parameter in the equations (1) and (2).

TABLE 1 definition of notations in Morgan model and values used in simulated calculation

| notation | definition/unit | value |
|---|---|---|
| C | Speed of sound in liquid/m · s$^{-1}$ | 1540 |
| ρ | Liquid density/kg · m$^{-3}$ | 998 |
| P$_0$ | Hydrostatic pressure/kPa | 101 |
| σ | Interfacial tension coefficient/N · m$^{-1}$ | 0.051 |
| ε | Thickness of lipid shell/nm | 1 |
| R$_0$ | Initial bubble radius/μm | 1.25 |
| γ | Polytropic gas exponent | 1.07 |
| μ | Liquid viscosity/Pa · s | 0.001 |
| χ | Elasticity modulus of lipid shell/N · m$^{-1}$ | 0.26 |
| εμ$_{sh}$ | Product of shell thickness and viscosity | 2.865 |
| P$_{driv}$(t) | Driving acoustic pressure | |
| R | Instantaneous bubble radius | |

Step (2): automatically emitting wide beam RF signals, and receiving the wide beam RF signals which are reflected back by an object, by ultrasound array transducers; and processing the wide beam RF signals with phase 0/180 which are received by the ultrasound array transducers, with a wavelet correlation analysis based on the mother wavelets obtained in the step (1); extracting a maximum wavelet correlation coefficient at an optimal wavelet transform scale; and constructing a PIW images matrix.

Figure 2:
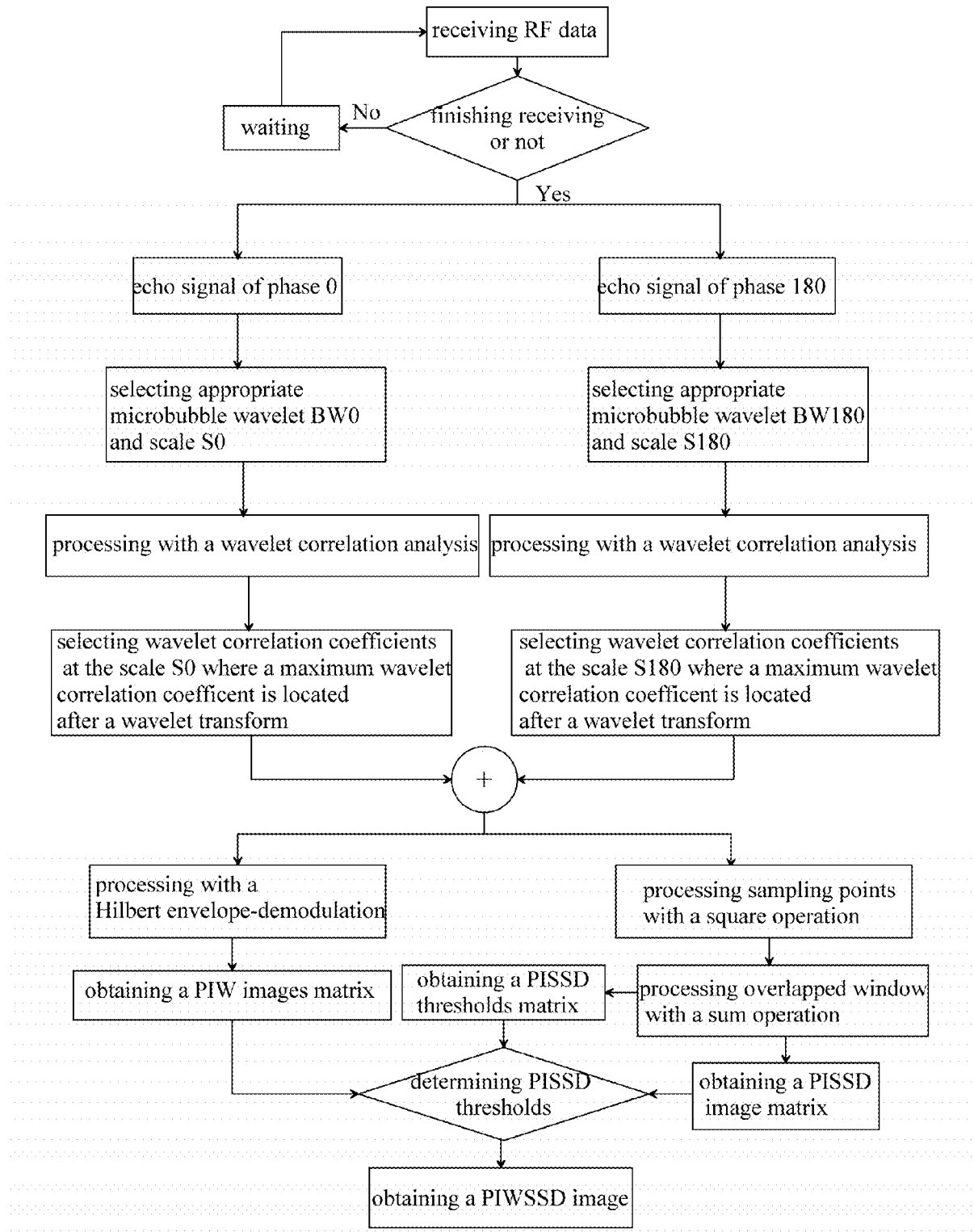
FIG. 2 is a flow chart of the pulse inversion wavelet transform decorrelation wide beam contrast imaging method according to the preferred embodiment of the present invention.

Referring to FIG. 2, the step (2) comprises steps of:

(d) at a finish of receiving the wide beam RF signals, selecting an appropriate scale according to experience, and respectively processing echo signals of the original RF signals of the phase 0 and the phase 180 with the wavelet correlation analysis based on the microbubble mother wavelets of the phase 0/180 constructed in the step (1), so as to obtain a series of the wavelet correlation coefficients;

(e) for the echo signals of the phase 0 and the phase 180, respectively selecting all wavelet correlation coefficients, at the scale where the maximum wavelet correlation coefficient is located, to be return values for denominating the echo signals of the original RF signals of the phase 0 and the phase 180; and (f) summing the wavelet correlation coefficients for denominating the echo signals of the original RF signals in the echo signals of the phase 0 and the phase 180, and obtaining the PIW images matrix via a Hilbert envelope-demodulation.

Step (3): constructing a pulse inversion sum squared differences (PISSD) thresholds matrix, determining decorrelation thresholds of the PIW images matrix obtained in the step (2), and then obtaining a PIWSSD image under the wide beam with a high CTR.

Referring to FIG. 2, the step (3) comprises steps of:

(g) dividing the echo signals denominated by the wavelet correlation coefficients of the phase 0 and the phase 180, obtained by the step (2), into a plurality of sampling windows, wherein each sampling window has a length of L$_w$ and is mutually overlapped by an overlap length of L$_o$;

(h) providing a PISSD algorithm showed as equation (3), wherein the PISSD thresholds matrix is determined by a total number of sampling points N, an ordinal number of the sampling windows n, the length of each sampling window L$_w$, the overlap length of each sampling window L$_o$, a sampling window function w[ ] and the wavelet correlation coefficients of the phase 0 and the phase 180:

$$PISSD(n) = \frac{1}{L_w} \sum_{k=1+(n-1)\Delta}^{L_o+n\Delta} (w[s_{f1}(k)] + w[s_{f2}(k)]])^2 \tag{3}$$

$$n = 1, 2, \ldots, (N - L_w)/\Delta + 1, \Delta = L_w - L_o, L_o < L_w,$$

wherein $s_{f1}(k)$ and $s_{f2}(k)$ are respectively the echo signals denominated by the wavelet correlation coefficients of the phase 0 and the phase 180 obtained by the step (2);

(i) constructing a two-dimensional PISSD thresholds matrix which illustrates a decorrelation degree of a tissue background, with the PISSD algorithm of step (h);

(j) defining four types of thresholds based on the PISSD thresholds matrix: a uniform threshold, a divided threshold, a lower combined threshold and a higher combined threshold; wherein:

the uniform threshold (UT) is a sum of a mean and a standard deviation of the PISSD matrix;

the PISSD matrix is divided into M sections with the same size along a scanning beam direction, the sum of the mean and the standard deviation of PISSD values within each section is the divided threshold (DT) corresponding to each section;

the lower combined threshold (LCT) is showed in equation (4):

$$LCT(i, j) = \begin{cases} DT(i, j), & DT(i, j) \leq UT \\ UT, & DT(i, j) > UT \end{cases} \quad (4)$$

$$i = 1, 2, \ldots, N_s, j = 1, 2, \ldots, N_l;$$

and the higher combined threshold (HCT) is showed in equation (5):

$$HCT(i, j) = \begin{cases} DT(i, j), & DT(i, j) \geq UT \\ UT, & DT(i, j) < UT \end{cases} \quad (5)$$

$$i = 1, 2, \ldots, N_s, j = 1, 2, \ldots, N_l;$$

(k) based on the four types of thresholds of the step (j), inputting the PISSD thresholds matrix, a PISSD images matrix and the PIW images matrix into a PISSD threshold determining module, and then obtaining the PIWSSD image.

Further, based on the PIWSSD image, the present invention provides a method for extracting a perfusion TIC, comprising the following steps.

Step (4): extracting a perfusion evaluation curve TIC of a ROI of the PIWSSD image of the step (3).

Step (5): constructing a window length order matrix X and a polynomial fitting coefficient matrix Fit for DFA.

The step (5) comprises steps of:

(l) determining the window length order matrix X for the DFA by a length of original TIC data Num, a DFA semi-window-length N and a polynomial fitting order K, and constructing the window length order matrix X for the DFA according to equation (6):

$$X = \begin{bmatrix} x(1)^0 & x(1)^1 & \cdots & x(1)^K \\ \vdots & \vdots & \ddots & \vdots \\ x(2N)^0 & x(2N)^1 & \cdots & x(2N)^K \\ x(2N+1)^0 & x(2N+1)^1 & \cdots & x(2N+1)^K \end{bmatrix}; \quad (6)$$

and (m) determining the polynomial fitting coefficient matrix Fit for the DFA by the length of the original TIC data Num and the DFA semi-window-length N; obtaining an optimal polynomial fitting coefficient matrix P of sections of TIC data with a least squares multiple regression analysis, according to equation (7):

$$P = (X^T X)^{-1} \times X^T \times \begin{bmatrix} TIC(1) & \cdots & TIC(2N) & TIC(2N+1) \\ TIC(N+1) & \cdots & TIC(3N) & TIC(3N+1) \\ \vdots & \ddots & \vdots & \vdots \\ TIC(Num-2N) & \cdots & TIC(Num-1) & TIC(Num) \end{bmatrix}; \quad (7)$$

and obtaining the polynomial fitting coefficient matrix Fit for the DFA according to equation (8):

$$\text{Fit} = X \times P \quad (8)$$

$$= X(X^T X)^{-1} \times$$

$$X^T \times \begin{bmatrix} TIC(1) & \cdots & TIC(2N) & TIC(2N+1) \\ TIC(N+1) & \cdots & TIC(3N) & TIC(3N+1) \\ \vdots & \ddots & \vdots & \vdots \\ TIC(Num-2N) & \cdots & TIC(Num-1) & TIC(Num) \end{bmatrix}.$$

Step (6): processing the TIC obtained by the step (4), with the DFA to extract a TIC tendency; providing control groups of a medium filtering and a polynomial fitting as a contrast, for evaluating the extracting.

Figure 3:
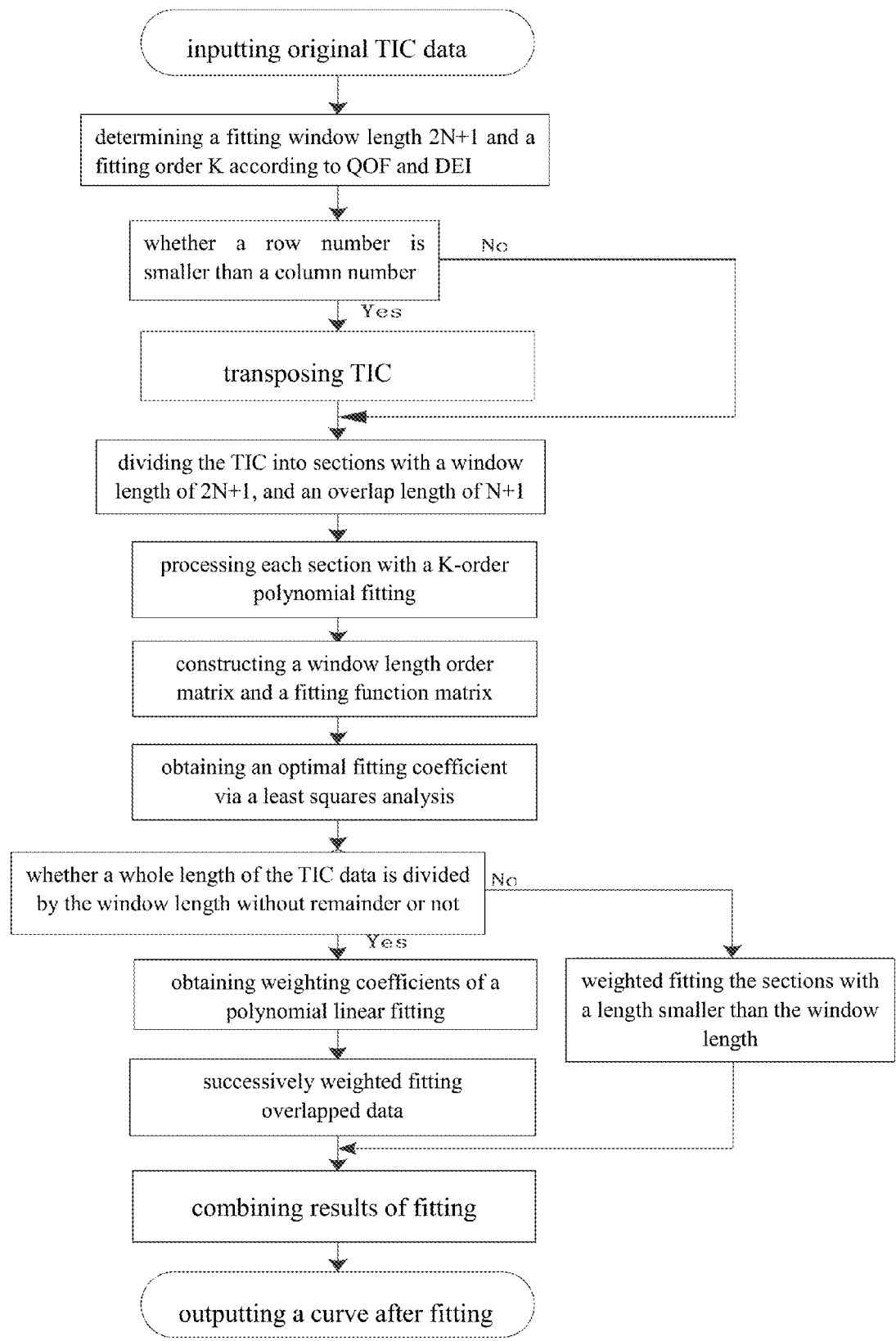
FIG. 3 is a flow chart of a rapid calculation of accurately extracting a wide beam contrast imaging-TIC tendency (DFA) according to the preferred embodiment of the present invention.

Referring to FIG. 3, the step (6) comprises steps of:

(n) judging a rank of the original TIC data to ensure that a row number is larger than a column number, and transposing the original TIC data when the row number of the original TIC data is smaller than the column number of the original TIC data;

(o) dividing the TIC data obtained by the step (n) into 2N+1 (marked as a window length) sections with the same length, wherein each two neighboring sections have N+1 points overlapped;

(p) for each section, selecting optimal K-order polynomials for fitting, wherein a constant and a linear fitting respectively correspond to K=0 and K=1;

(q) constructing the window length order matrix X and the polynomial fitting coefficient matrix Fit for the DFA, as showed in the equations (6), (7) and (8);

(r) obtaining the optimal polynomial fitting coefficient matrix P of the sections of the TIC data with the least squares multiple regression analysis, as showed in the equation (7);

(s) judging whether a whole length of the TIC data is divided by the window length without remainder; if without remainder, obtaining a weighting coefficient of the polynomial linear fitting; if with remainder, firstly weighted fitting a last section of the TIC data whose length is smaller than the window length;

(t) respectively marking the fitted polynomials of the ith section and the (i+1)th section as $y^i(l_1)$ and $y^{i+1}(l_2)$, $l_1, l_2=1, \ldots, 2N+1$;

wherein the fitted polynomial of the overlapped section $y^o(l)$ is $y^o(l) = w_1 y^i(l+N) + w_2 y^{i+1}(l)$, $l=1, \ldots, N+1$, wherein the weighting coefficients of the polynomial linear fitting are respectively $w_1 = 1-(l-1)/N$, $w_2 = (l-1)/N$;

(u) successively weighted fitting the data of the overlapped section, wherein the weighting coefficients ensure a symmetry and are able to well eliminate data jump or discontinuity at an overlapped part of the two neighboring sections (section boundary); and (v) combining results of weighted fitting the last section of the TIC data whose length is smaller than the window length and the sections therebefore, and outputting a TIC after fitting.

QOF and DEI are defined by the TIC obtained in the step (6), for evaluating a fitting quality; a runtime is calculated via tic and toc methods of matlab, for evaluating a calculation speed, which specifically comprises steps of:

(w) selecting a quality of fitting (QOF) as a first evaluation index of an overall tendency of the TIC; wherein the QOF is defined according to equations (9), (10) and (11):

$$QOF = \left(1 - \frac{SSR_f}{VAR_d}\right) \times 100\%; \quad (9)$$

$$SSR_f = \sum_{t=t_{start}}^{t_{end}} (TIC_f(t) - TIC_d(t))^2; \text{ and} \quad (10)$$

$$VAR_d = \sum_{t=t_{start}}^{t_{end}} \left(TIC_d(t) - \frac{\sum_{t=t_{start}}^{t_{end}} TIC_d(t)}{N}\right)^2; \quad (11)$$

wherein $SSR_f$ is a sum squared residue of the TIC after fitting and a filtering TIC within a fitting interval; $VAR_d$ is a variance of the filtering TIC within the fitting interval; $TIC_f$ is the TIC after fitting and $TIC_d$ is the filtering TIC; $t_{start}$ and $t_{end}$ are a starting point and an ending point of the fitting interval; and N is a number of the sample points within the fitting interval;

wherein the QOF is a percent and inversely proportional to $SSR_f$; the smaller $SSR_f$, the larger QOF; when $SSR_f$=0, QOF reaches 100%, namely the TIC has a best fitting quality; when QOF is lower than 80%, the TIC is inaccurately fitted and thus lacks reliability;

(x) selecting a detailed evaluation index (DEI) as a second evaluation index of the overall tendency of the TIC; wherein the DEI is defined as:

$$DEI = \frac{\sum(|TIC_f(t) - TIC_f(t-1)| + |TIC_f(t) - TIC_f(t+1)|)}{\sum(|TIC_d(t) - TIC_d(t-1)| + |TIC_d(t) - TIC_d(t+1)|)}, \quad (12)$$

wherein $TIC_f(t)$ and $TIC_d(t)$ are respectively TIC values before fitting and after fitting; a maximum of the DEI is 1, and a minimum of the DEI is 0; the larger DEI indicates the stronger ability of the TIC after fitting to preserve details of the original data; when the DEI is smaller than 0.85, the TIC after fitting distorts against perfusion details and thus lacks reliability;

(y) coding via matlab for calculating the QOF and the DEI; and (z) respectively processing the TIC data with the DFA and the medium filtering, and calculating out the QOF, the DEI and the runtime.

Figure 4:
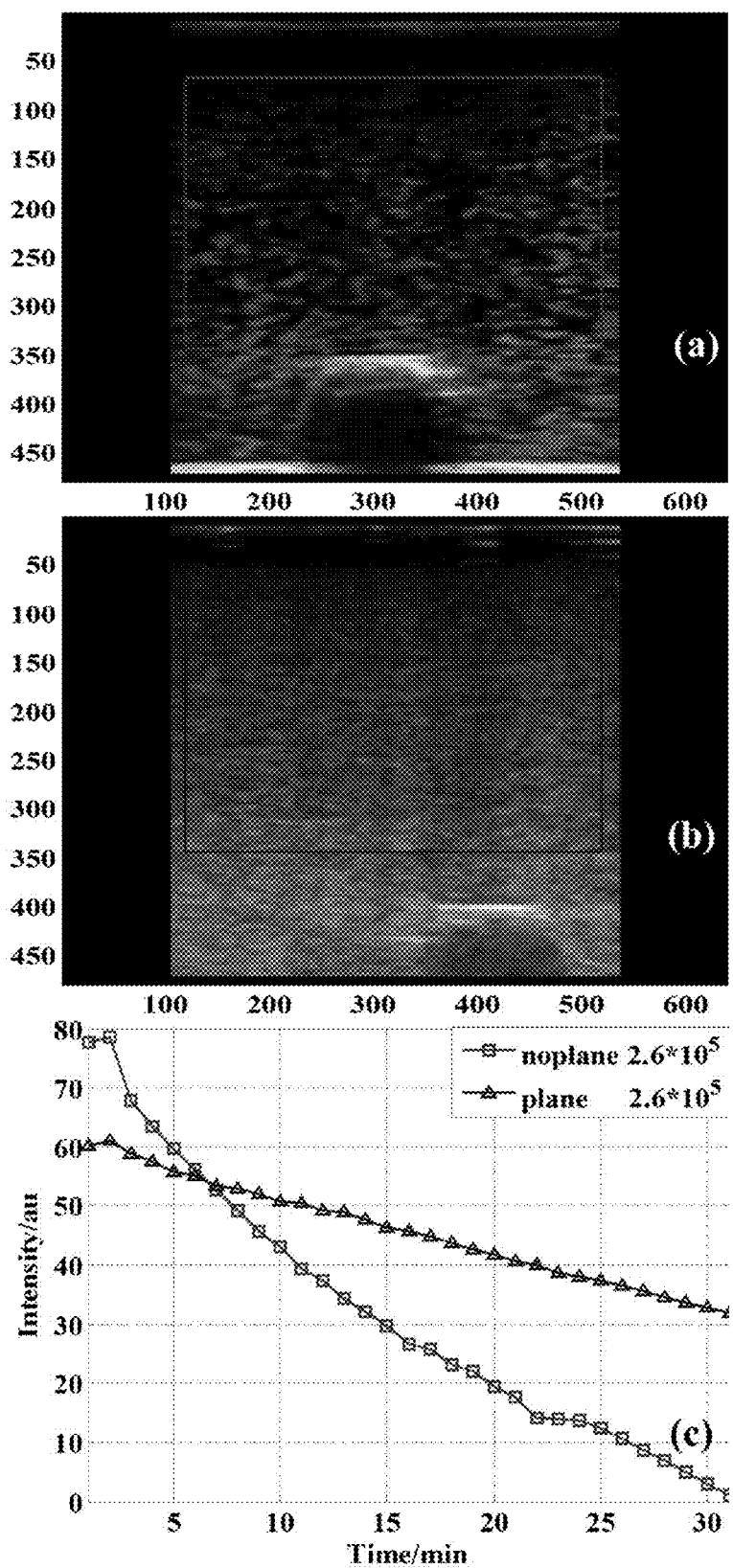
FIG. 4 is a comparison diagram about static attenuation between contrast microbubbles exited by a wide beam and the contrast microbubbles excited by a narrow beam.

Referring to FIG. 4, under an action of a magnetic stir bar, an ultrasound with an emitted center frequency of 5 MHz is applied onto 600 ml of SonoVue with a concentration of 1%, diluted 1000 times, so as to respectively obtain contrast images, FIGS. 4a and 4b, via a narrow beam and a wide beam through scanning line by line, and respectively extract the TICs (FIG. 4c) of the identically sized regions of interest from the two contrast images. It is showed that the two curves decrease with the time, resulting from the damage on the microbubbles by the acoustic beam and free disruption of the microbubbles. Compared to the curve of the wide beam, the curve of the narrow beam has a higher origin point and decreases faster, which proves that the narrow beam has a higher emitted power and exerts worse destruction onto the microbubbles by causing multiple times of damages.

Figure 5:
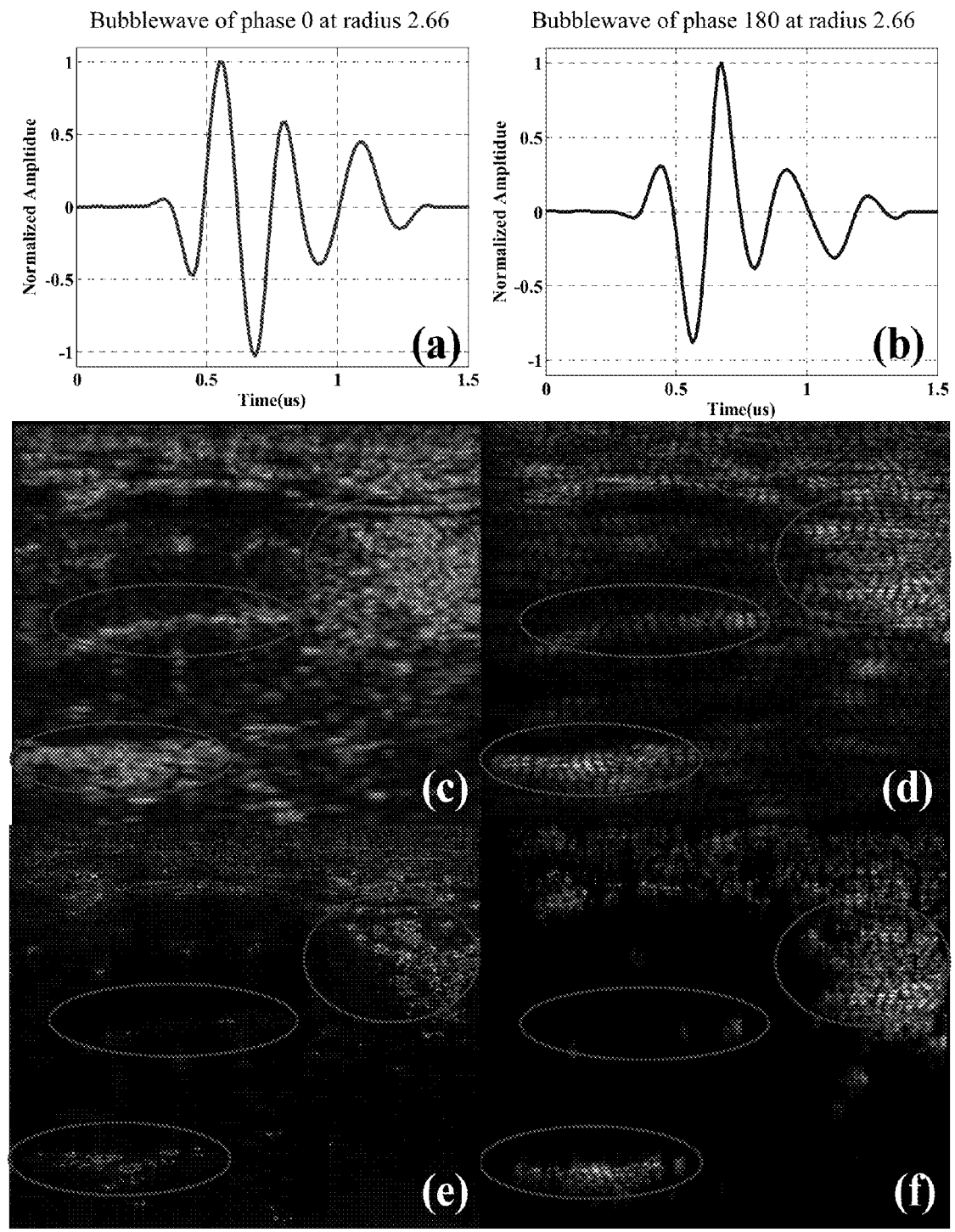
FIG. 5 shows pulse inversion wavelet transform decorrelation wide beam imaging results in vivo using kidneys of rabbits according to the preferred embodiment of the present invention.

Referring to FIG. 5, the pulse inversion wavelet transform decorrelation wide beam contrast imaging results in vivo using kidneys of rabbits weighed 3.3 kg. FIGS. 5a and 5b respectively show the mother wavelets of the compression phase and the expansion phase (phase 0/180) for the wide beam contrast imaging; FIGS. 5c, 5d, 5e and 5f are respectively images of original pulse inversion imaging, pulse inversion microbubble transform imaging, pulse inversion decorrelation imaging and pulse inversion wavelet transform decorrelation imaging. It is indicated that the four images respectively have some preservation within three circles which are reckoned to be a kidney internal vessel region and a kidney external vessel region with blood flow information, leaving other regions gradually eliminated from FIG. 5c to FIG. 5f. The eliminated regions are reckoned to be tissues with little movement information. It is showed from FIG. 5c to FIG. 5f that the CTR increases gradually, which means that the pulse inversion wavelet transform decorrelation imaging method owns higher imaging quality than the former three imaging methods under the wide beam.

Figure 6:
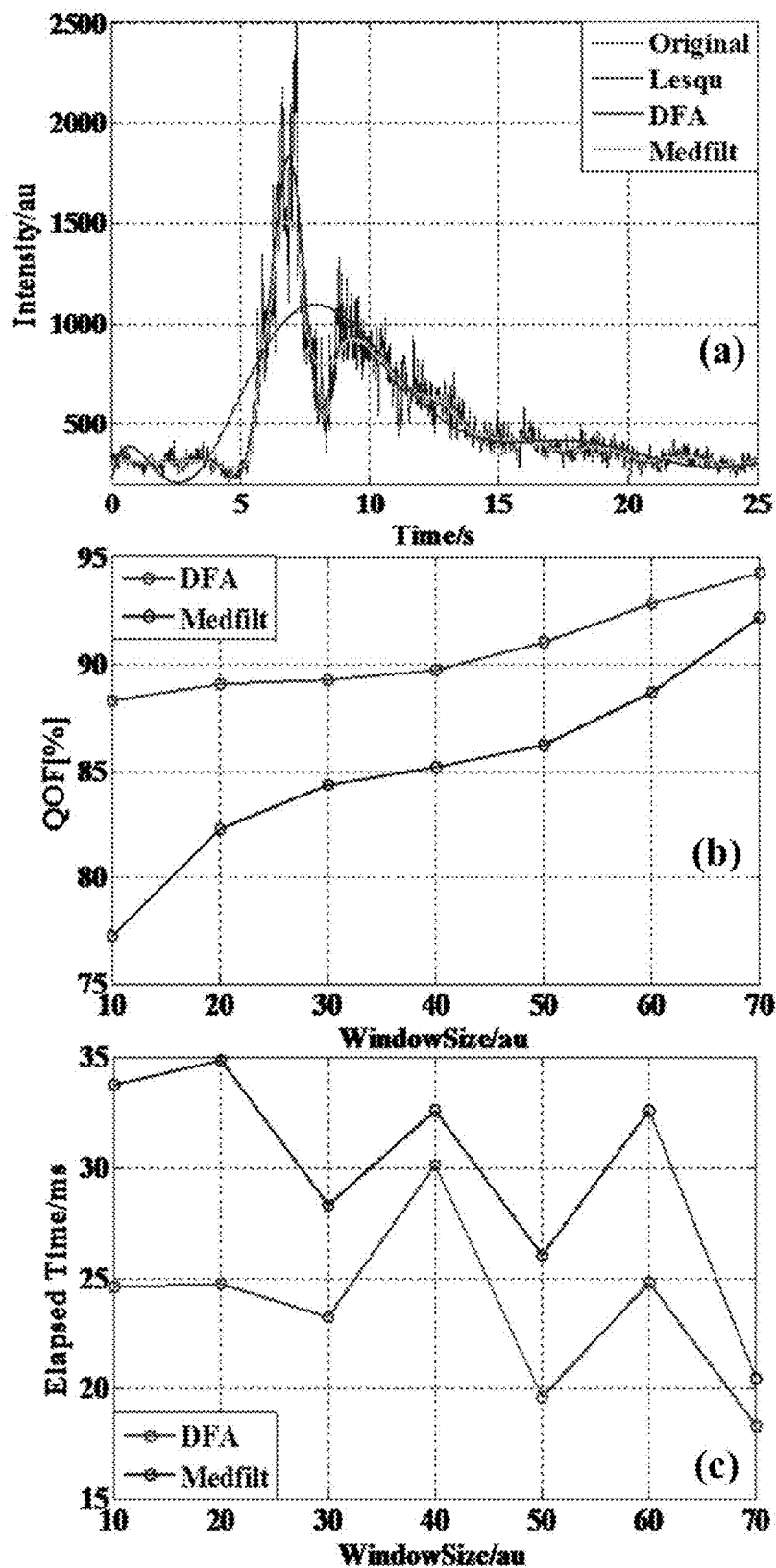
FIG. 6 shows comparisons between the DFA and medium filtering of Ø3 mm tube TIC in results, fitting coefficients and runtime.

FIG. 6a of FIG. 6 shows comparison among the original TIC data, a tenth-order polynomial fitting curve, a curve obtained via the DFA with the window length of 60 and a curve obtained via the medium filtering. An integral extract of the polynomial fitting curve merely generates a very rough TIC tendency which almost displays no detailed information. From the DFA fitting and the medium filtering are both able to extract out the TIC overall tendencies; the DFA fitting has a stronger detail display capability, while the medium filtering shows unreal smooth data at important peaks and valleys. Referring to FIG. 6b, at a range of the window length from 10 to 70, under the same window length, the QOF of the DFA is 6% higher than the QOF of the medium filtering on average; when the window length is 10, the QOF of the medium filtering falls below 80% and lacks reliability. Referring to FIG. 6c, at the range of the window length from 10 to 70, the calculation time of the DFA is 6.3 ms shorter than the calculation time of the medium filtering. Speaking from the two aspects of the QOF and the calculation time, the DFA is superior to the medium filtering in the fitting quality and the calculation speed.

What is claimed is:

1. A contrast imaging method based on a wide beam, comprising steps of:
    (1) constructing microbubble mother wavelets of phase 0/180 for a wide beam contrast imaging, according to a Herring-Trilling microbubble oscillation equation modified by Morgan model;
    (2) automatically emitting wide beam radio frequency (RF) signals, and receiving the wide beam RF signals which are reflected back by an object, by ultrasound array transducers; processing the wide beam RF signals of phase 0/180 which are received by the ultrasound array transducers, with a wavelet correlation analysis based on the microbubble mother wavelets obtained by the step (1); extracting a maximum wavelet correlation coefficient at an optimal wavelet transform scale; and constructing a pulse inversion microbubble wavelet transform (PIW) images matrix; and
    (3) constructing a pulse inversion sum squared differences (PISSD) thresholds matrix, determining decorrelation thresholds of the PIW images matrix obtained by the step (2), and obtaining a pulse inversion microbubble wavelet transform sum squared differences decorrelation (PIWSSD) image of the wide beam contrast imaging.

2. The contrast imaging method based on the wide beam, as recited in claim 1, wherein the step (1) comprises steps of:
    (a) driving the Herring-Trilling microbubble oscillation equation, showed as an equation (1), respectively with scanning acoustic pressure curves of phase 0/180 with the wide beam; then obtaining a change curve of a microbubble oscillation radius with time, a corresponding radial oscillation velocity and a corresponding acceleration;

(b) substituting the obtained change curve, the radial oscillation velocity and the acceleration into an equation (2) to obtain a microbubble oscillation amplitude acoustic pressure waveform under the wide beam; and (c) processing the microbubble oscillation amplitude acoustic pressure waveform under the wide beam, into the microbubble mother wavelets of the phase 0/180 for the wide beam contrast imaging, through a band-pass filtering and a normalization;

$$\rho \dot{R}\ddot{R} + \frac{3}{2}\rho \dot{R}^2 = \qquad (1)$$

$$\left[P_0 + \frac{2\sigma}{R_0} + \frac{2\chi}{R_0}\right]\left[\frac{R_0}{R}\right]^{3\gamma}\left[1 - \frac{3\gamma}{c}\dot{R}\right] - \frac{4\mu\dot{R}}{R} - \frac{2\sigma}{R}\left[1 - \frac{1}{c}\dot{R}\right] -$$

$$\frac{2\chi}{R}\left(\frac{R_0}{R}\right)^2\left(1 - \frac{3}{c}\dot{R}\right) - 12\mu_{sh}\varepsilon\frac{\dot{R}}{R(R\cdot\varepsilon)} - [P_0 + P_{driv}(t)],$$

and $$P = \rho r^{-1}(R^2\ddot{R} + R\dot{R}^2) \qquad (2).$$

3. The contrast imaging method based on the wide beam, as recited in claim 1, wherein the step (2) comprises steps of:

(d) at a finish of receiving the wide beam RF signals, selecting an appropriate scale, and respectively processing echo signals of the RF signals of phase 0 and phase 180 with the wavelet correlation analysis based on the microbubble mother wavelets of the phase 0/180 constructed in the step (1), so as to obtain a series of wavelet correlation coefficients;

(e) for the echo signals of the phase 0 and the phase 180, respectively selecting all wavelet correlation coefficients, at the scale where the maximum wavelet correlation coefficient is located, to be return values for denominating the echo signals of the RF signals of the phase 0 and the phase 180; and (f) summing the wavelet correlation coefficients for denominating the echo signals of the RF signals in the echo signals of the phase 0 and the phase 180, and obtaining the PIW images matrix via a Hilbert envelope-demodulation.

4. The contrast imaging method based on the wide beam, as recited in claim 3, wherein the step (3) comprises steps of:

(g) dividing the echo signals denominated by the wavelet correlation coefficients of the phase 0 and the phase 180, obtained by the step (2), into a plurality of sampling windows, wherein each sampling window has a length of $L_w$ and is mutually overlapped by an overlap length of $L_o$;

(h) providing a PISSD algorithm showed as equation (3), wherein the PISSD thresholds matrix is determined by a total number of sampling points N, an ordinal number of the sampling windows n, the length of each sampling window $L_w$, the overlap length of each sampling window $L_o$, a sampling window function w[ ] and the wavelet correlation coefficients of the phase 0 and the phase 180:

$$PISSD(n) = \frac{1}{L_w}\sum_{k=1+(n-1)\Delta}^{L_o+n\Delta}(w[s_{f1}(k)] + w[s_{f2}(k)])^2 \qquad (3)$$

$n = 1, 2, \ldots, (N-L_w)/\Delta + 1, \Delta = L_w - L_o, L_o < L_w,$ wherein $s_{f1}(k)$ and $s_{f2}(k)$ are respectively the echo signals denominated by the wavelet correlation coefficients of the phase 0 and the phase 180 obtained by the step (2);

(i) constructing a two-dimensional PISSD thresholds matrix which illustrates a decorrelation degree of a tissues background, with the PISSD algorithm of step (h);

(j) defining four types of thresholds based on the PISSD thresholds matrix: a uniform threshold, a divided threshold, a lower combined threshold and a higher combined threshold; wherein:

the uniform threshold is a sum of a mean and a standard deviation of the PISSD matrix;

the PISSD matrix is divided into M sections with the same size along a scanning beam direction, the sum of the mean and the standard deviation of PISSD within each section is the divided threshold corresponding to each section;

the lower combined threshold (LCT) is showed in equation (4):

$$LCT(i, j) = \begin{cases} DT(i, j), & DT(i, j) \leq UT \\ UT, & DT(i, j) > UT \end{cases} \qquad (4)$$

$i = 1, 2, \ldots, N_s, \quad j = 1, 2, \ldots, N_l;$ and the higher combined threshold (HCT) is showed in equation (5):

$$HCT(i, j) = \begin{cases} DT(i, j), & DT(i, j) \geq UT \\ UT, & DT(i, j) < UT \end{cases} \qquad (5)$$

$i = 1, 2, \ldots, N_s, \quad j = 1, 2, \ldots, N_l;$ (k) based on the four types of thresholds of the step (j), inputting the PISSD thresholds matrix, a PISSD images matrix and the PIW images matrix into a PISSD threshold determining module, and then obtaining the PIWSSD image.

5. A method for extracting a perfusion time-intensity curve (TIC) of the contrast imaging method based on the wide beam as recited in claim 1, further comprising steps of:

(4) extracting a perfusion TIC of a region of interest (ROI) of the PIWSSD image of the step (3);

(5) constructing a window length order matrix X and a polynomial fitting coefficient matrix Fit for a detrended fluctuation analysis (DFA); and (6) processing the TIC, obtained in the step (4), with the DFA to extract a TIC tendency.

6. The method for extracting the perfusion TIC, as recited in claim 5, wherein the step (5) comprises steps of:

(l) determining the window length order matrix X for the DFA by a length of original TIC data Num, a DFA semi-window-length N and a polynomial fitting order K, and constructing the window length order matrix X for the DFA according to equation (6):

$$X = \begin{bmatrix} x(1)^0 & x(1)^1 & \cdots & x(1)^K \\ \vdots & \vdots & \ddots & \vdots \\ x(2N)^0 & x(2N)^1 & \cdots & x(2N)^K \\ x(2N+1)^0 & x(2N+1)^1 & \cdots & x(2N+1)^K \end{bmatrix}; \quad (6)$$

and (m) determining the polynomial fitting coefficient matrix Fit for the DFA by the length of the original TIC data Num and the DFA semi-window-length N; obtaining an optimal polynomial fitting coefficient matrix P of sections of TIC data with a least-squares multiple regression analysis, according to equation (7):

$$P = (X^T X)^{-1} \times X^T \times \begin{bmatrix} TIC(1) & \cdots & TIC(2N) & TIC(2N+1) \\ TIC(N+1) & \cdots & TIC(3N) & TIC(3N+1) \\ \vdots & \ddots & \vdots & \vdots \\ TIC(Num-2N) & \cdots & TIC(Num-1) & TIC(Num) \end{bmatrix}; \quad (7)$$

and obtaining the polynomial fitting coefficient matrix Fit for the DFA according to equation (8):

$$Fit = X \times P \quad (8)$$
$$= X(X^T X)^{-1} \times$$
$$X^T \times \begin{bmatrix} TIC(1) & \cdots & TIC(2N) & TIC(2N+1) \\ TIC(N+1) & \cdots & TIC(3N) & TIC(3N+1) \\ \vdots & \ddots & \vdots & \vdots \\ TIC(Num-2N) & \cdots & TIC(Num-1) & TIC(Num) \end{bmatrix}.$$

7. The method for extracting the perfusion TIC, as recited in claim 6, wherein the step (6) comprises steps of
(n) judging a rank of the original TIC data to ensure that a row number is larger than a column number, and transposing the original TIC data when the row number of the original TIC data is smaller than the column number of the original TIC data;
(o) dividing the transposed TIC data obtained by the step (n) into 2N+1 sections with the same length, and marking the length of the 2N+1 sections as a window length, wherein each two neighboring 2N+1 sections have N+1 points overlapped;
(p) for each 2N+1 section, selecting optimal K-order polynomials for fitting, wherein a constant and a linear fitting respectively correspond to K=0 and K=1;
(q) constructing the window length order matrix X and the polynomial fitting coefficient matrix Fit for the DFA;
(r) obtaining the optimal polynomial fitting coefficient matrix P of the sections of the TIC data with the least squares multiple regression analysis;
(s) judging whether a whole length of the TIC data is divided by the window length without remainder; if without remainder, obtaining a weighting coefficient of the polynomial linear fitting; if with remainder, firstly weighted fitting a last section of the TIC data whose length is smaller than the window length;
(t) respectively marking the fitted polynomials of an ith section and an (i+1)th section as $y^i(l_1)$ and $y^{i+1}(l_2)$, $l_1, l_2 = 1, \ldots, 2N+1$;

wherein the fitted polynomial of an overlapped section $y^o(l)$ is $y^o(l) = w_1 y^i(l+N) + w_2 y^{i+1}(l)$, $l=1, \ldots, N+1$, wherein the weighting coefficient of the polynomial linear fitting is respectively $w_1 = 1-(l-1)/N$, $w_2 = (l-1)/N$;
(u) successively weighted fitting data of the overlapped section; and
(v) combining results of weighted fitting the last section of the TIC data whose length is smaller than the window length and the sections therebefore, and outputting a TIC after fitting.

8. The method for extracting the perfusion TIC, as recited in claim 7, further comprising a step of evaluating a quality of fitting of the TIC after fitting, which comprises steps of
(w) selecting a quality of fitting (QOF) as a first evaluation index of an overall tendency of the TIC after fitting;
(x) selecting a detailed evaluation index (DEI) as a second evaluation index of the overall tendency of the TIC after fitting;
(y) coding via matlab for calculating the QOF and the DEI; and
(z) respectively processing the TIC data with the DFA, and calculating out the QOF, the DEI and a runtime.

9. The method for extracting the perfusion TIC, as recited in claim 8, wherein when the QOF reaches a maximum value of 100%, the TIC after fitting is best fitted; when the QOF is lower than 80%, the TIC after fitting is inaccurately fitted and thus lacks reliability; and
the QOF is calculated according to equations (9), (10) and (11):

$$QOF = \left(1 - \frac{SSR_f}{VAR_d}\right) \times 100\%; \quad (9)$$

$$SSR_f = \sum_{t=t_{start}}^{t_{end}} (TIC_f(t) - TIC_d(t))^2; \text{ and} \quad (10)$$

$$VAR_d = \sum_{t=t_{start}}^{t_{end}} \left(TIC_d(t) - \frac{\sum_{t=t_{start}}^{t_{end}} TIC_d(t)}{N}\right)^2; \quad (11)$$

wherein $SSR_f$ is a sum squared residue of the TIC after fitting and a filtering TIC within a fitting interval; $VAR_d$ is a variance of the filtering TIC within the fitting interval; $TIC_f$ is the TIC after fitting and $TIC_d$ is the filtering TIC; $t_{start}$ and $t_{end}$ are a starting point and an ending point of the fitting interval; and N is a number of sample points within the fitting interval.

10. The method for extracting the perfusion TIC, as recited in claim 8, wherein a larger DEI indicates a stronger ability of the TIC after fitting to preserve details of the original data; when the DEI is smaller than 0.85, the TIC after fitting distorts against perfusion details and thus lacks reliability; and
the DEI is defined as:

$$DEI = \frac{\sum (|TIC_f(t) - TIC_f(t-1)| + |TIC_f(t) - TIC_f(t+1)|)}{\sum (|TIC_d(t) - TIC_d(t-1)| + |TIC_d(t) - TIC_d(t+1)|)}, \quad (12)$$

wherein $TIC_f(t)$ and $TIC_d(t)$ are respectively TIC values before fitting and after fitting; a maximum of the DEI is 1, and a minimum of the DEI is 0.

* * * * *